United States Patent [19]

Sih

[11] 4,283,558

[45] Aug. 11, 1981

[54] 2-DECARBOXY-2-AMINOMETHYL-19-HYDROXY-PG COMPOUNDS

[75] Inventor: John C. Sih, Kalamazoo, Mich.

[73] Assignee: The Upjohn Company, Kalamazoo, Mich.

[21] Appl. No.: 88,662

[22] Filed: Oct. 26, 1979

Related U.S. Application Data

[62] Division of Ser. No. 25,899, Apr. 2, 1979, Pat. No. 4,228,104.

[51] Int. Cl.³ .............................................. C07C 87/50
[52] U.S. Cl. ................................................. 564/305
[58] Field of Search ......................................... 564/305

[56] References Cited

U.S. PATENT DOCUMENTS 4,228,104  10/1980  Sih ........................................ 568/379

*Primary Examiner*—Robert V. Hines
*Attorney, Agent, or Firm*—Lawrence T. Welch; Robert A. Armitage

[57] ABSTRACT

The present invention provides novel 2-decarboxy-2-hydroxymethyl-19,20-didehydro-13,14-dihydro-$PG_1$ compounds methods for their preparation and pharmacological use for the induction of prostaglandin-like effect.

263 Claims, No Drawings

2-DECARBOXY-2-AMINOMETHYL-19-HYDROXY-PG COMPOUNDS

CROSS REFERENCE TO RELATED APPLICATIONS

The present application is a division of Ser. No. 025,899, filed Apr. 2, 1979, now U.S. Pat. No. 4,228,104.

DESCRIPTION

1. Background of the Invention

The present invention relates to novel prostaglandin analogs. Particularly, these compounds are analogs of the prostaglandins wherein the C-19 position is substituted by hydroxy, i.e., 19-hydroxy-PG compounds. Most particularly, the present invention relates to novel 2-decarboxy-2-aminomethyl-19-hydroxy-PG compounds, a disclosure of the preparation and use of which is incorporated here by reference from U.S. Pat. No. 4,228,104.

2. Prior Art

Prostaglandin analogs exhibiting hydroxylation in the 19-position are known in the art. See, for example, U.S. Pat. No. 4,127,612, Sih, J. C., Prostaglandins 13:831 (1977) and U.S. Pat. Nos. 3,657,316, 3,878,046, and 3,922,297. See also the additional references cited in United States Ser. No. 025,899.

SUMMARY OF THE INVENTION

The present invention particularly provides:
A compound of the formula

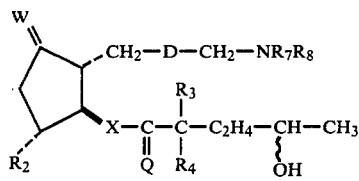

wherein D is
(1) cis-CH=CH—CH$_2$—(CH$_2$)$_g$—CH$_2$—,
(2) cis-CH=CH—CH$_2$—(CH$_2$)$_g$—CF$_2$—,
(3) cis-CH$_2$—CH=CH—CH$_2$—CH$_2$—,
(4) trans-(CH$_2$)$_3$—CH=CH—,
(5) —(CH$_2$)$_3$—(CH$_2$)$_g$—CH$_2$—,
(6) —(CH$_2$)$_3$—CH$_2$—CF$_2$—,
(7) —(CH$_2$)$_3$—O—CH$_2$—,
(8) —(CH$_2$)$_2$—O—(CH$_2$)$_2$—,
(9) —CH$_2$—O—(CH$_2$)$_3$—,
(10) —(m-ph)—(CH$_2$)$_2$—, or
(11) —(m-ph)—O—CH$_2$—,
wherein m-ph is inter-meta-phenylene, and
wherein g is zero, one, two, or three;
wherein Q is $\alpha$-OH:$\beta$-R$_5$ or $\alpha$-R$_5$:$\beta$-OH,
wherein R$_5$ is hydrogen or methyl,
wherein R$_7$ and R$_8$ are hydrogen, alkyl of one to 12 carbon atoms, inclusive, benzyl, or phenyl, being the same or different;
wherein R$_2$ is hydrogen, hydroxyl, or hydroxymethyl;
wherein R$_3$ and R$_4$ are hydrogen, methyl, or fluoro, being the same or different, with the proviso that one of R$_3$ and R$_4$ is fluoro only when the other is hydrogen or fluoro;
wherein W is oxo, methylene, $\alpha$-OH:B-H, or $\alpha$-H:$\beta$-OH; and wherein X is cis- or trans-CH=CH—, —C≡C—, or —CH$_2$CH$_2$—.

With regard to the divalent the substituents described above (e.g., Q) these divalent radicals are defined as $\alpha$-R$_I$:$\beta$-R$_J$, wherein R$_I$ represents the substituent of the divalent moiety in the alpha configuration with respect to the ring and R$_j$ represents the substituent of the divalent moiety in the beta configuration with respect to the plane of the ring. Accordingly, when Q is defined as $\alpha$-OH:$\beta$-R$_5$, the hydroxy of the Q moiety is in the alpha configuration, i.e., as in the natural prostaglandin, and the R$_5$ substituent is in the beta configuration.

Specific embodiments of the present invention include:
2-decarboxy-2-aminomethyl-19(R)-19-hydroxyPGF$_{2\alpha}$,
2-decarboxy-2-aminomethyl-11-deoxy-19(R)-19-hydroxy-PGF$_{2\alpha}$,
2-decarboxy-2-aminomethyl-11-deoxy-11$\alpha$-hydroxymethyl-19(R)-19-hydroxy-PGF$_{2\alpha}$,
2-decarboxy-2-aminomethyl-19(R)-19-hydroxy-PGF$_{2\beta}$,
2-decarboxy-2-aminomethyl-11-deoxy-19(R)-hydroxyPGF$_{2\beta}$,
2-decarboxy-2-aminomethyl-11-deoxy-11$\alpha$-hydroxymethyl-19(R)-19-hydroxy-PGF$_{2\beta}$,
2-decarboxy-2-aminomethyl-19(R)-19-hydroxy-PGE$_2$,
2-decarboxy-2-aminomethyl-11-deoxy-19(R)-19-hydroxy-PGE$_2$,
2-decarboxy-2-aminomethyl-11-deoxy-11$\alpha$-hydroxy methyl-19(R)-19-hydroxy-PGE$_2$,
2-decarboxy-2-aminomethyl-9-deoxo-9-methylene-19(R)-19-hydroxy-PGE$_2$,
2-Decarboxy-2-aminomethyl-9-deoxo-9-methylene-11-deoxy-19(R)-19-hydroxy-PGE$_2$,
2-Decarboxy-2-aminomethyl-9-deoxo-9-methylene-11-deoxy-11$\alpha$-hydroxymethyl-19(R)-19-hydroxy-PGE$_2$,
2-decarboxy-2-aminomethyl-4,5-didehydro-19(R)-19-hydroxy-PGF$_{1\alpha}$,
2-decarboxy-2-aminomethyl-4,5-didehydro-19(R)-19-hydroxy-15(S)-15-methyl-PGF$_{1\alpha}$,
2-decarboxy-2-aminomethyl-4,5,13,14,-tetradehydro-19(R)-19-hydroxy-PGF$_{1\alpha}$,
2-decarboxy-2-aminomethyl-4,5,13,14-tetradehydro-19(R)-19-hydroxy-16,16-difluoro-PGF$_{1\alpha}$,
2-decarboxy-2-aminomethyl-4,5-didehydro-19(R)-19-hydroxy-11-deoxy-PGF$_{1\alpha}$,
2-decarboxy-2-aminomethyl-4,5-didehydro-19(R)-19-hydroxy-11-deoxy-15(S)-15-methyl-PGF$_{1\alpha}$,
2-decarboxy-2-aminomethyl-4,5,13,14-tetradehydro-19(R)-19-hydroxy-11-deoxy-PGF$_{1\alpha}$,
2-decarboxy-2-aminomethyl-4,5,13,14-tetradehydro-19(R)-19-hydroxy-11-deoxy-16,16-difluoro-PGF$_{1\alpha}$,
2-decarboxy-2-aminomethyl-4,5-dideoxy-19(R)-19-hydroxy-11-deoxy-11$\alpha$-hydroxymethyl-PGF$_{1\alpha}$,
2-decarboxy-2-aminomethyl-4,5-dideoxy-19(R)-19-hydroxy-11-deoxy-11$\alpha$-hydroxymethyl-15(S)-15-methyl-PGF$_{1\alpha}$,
2-decarboxy-2-aminomethyl-4,5,13,14-tetradehydro-19(R)-19-hydroxy-11-deoxy-11$\alpha$-hydroxymethyl-PGF$_{1\alpha}$,
2-decarboxy-2-aminomethyl-4,5,13,14-tetradehydro-19(R)-19-hydroxy-11-deoxy-11$\alpha$-hydroxymethyl-16,16-difluoro-PGF$_{1\alpha}$,
2-decarboxy-2-aminomethyl-4,5-didehydro-19(R)-19-hydroxy-PGF$_{1\alpha}$,
2-decarboxy-2-aminomethyl-4,5-didehydro-19(R)-19-hydroxy-15(S)-15-methyl-PGF$_{1\beta}$,
2-decarboxy-2-aminomethyl-4,5,13,14-tetradehydro-19(R)-19-hydroxy-PGF$_{1\beta}$,
2-decarboxy-2-aminomethyl-4,5,13,14-tetradehydro-19(R)-19-hydroxy-16,16-difluoro-PGF$_{1\beta}$, 2-decarboxy-2-aminomethyl-4,5-didehydro-19(R)-19-hydroxy-11-deoxy-PGF$_{1\beta}$,
2-decarboxy-2-aminomethyl-4,5-didehydro-19(R)-19-hydroxy-11-deoxy-15(S)-15-methyl-PGF$_{1\beta}$,
2-decarboxy-2-aminomethyl-4,5,13,14-tetradehydro-19(R)-19-hydroxy-11-deoxy-PGF$_{1\beta}$,
2-decarboxy-2-aminomethyl-4,5,13,14-tetradehydro-19(R)-19-hydroxy-11-deoxy-16,16-difluoro-PGF$_{1\beta}$,
2-decarboxy-2-aminomethyl-4,5-didehydro-19(R)-19-hydroxy-11-deoxy-11α-hydroxymethyl-PGF$_{1\beta}$,
2-decarboxy-2-aminomethyl-4,5-didehydro-19(R)-19-hydroxy-11-deoxy-11α-hydroxymethyl-15(S)-15-methyl-PGF$_{1\beta}$,
2-decarboxy-2-aminomethyl-4,5,13,14-tetradehydro-19(R)-19-hydroxy-11-deoxy-11α-hydroxymethyl-PGF$_{1\beta}$,
2-decarboxy-2-aminomethyl-4,5,13,14-tetradehydro-19(R)-19-hydroxy-11-deoxy-11α, hydroxymethyl-16,16-difluoro-PGF$_{1\beta}$,
2-decarboxy-2-aminomethyl-4,5-didehydro-19(R)-19-hydroxy-PGE$_1$,
2-decarboxy-2-aminomethyl-4,5-didehydro-19(R)-19-hydroxy-15(S)-15-methyl-PGE$_1$,
2-decarboxy-2-aminomethyl-4,5,13,14-tetradehydro-19(R)-19-hydroxy-PGE$_1$,
2-decarboxy-2-aminomethyl-4,5,13,14-tetradehydro-19(R)-19-hydroxy-16,16-difluoro-PGE$_1$,
2-decarboxy-2-aminomethyl-4,5-didehydro-19(R)-19-hydroxy-11-deoxy-PGE$_1$,
2-decarboxy-2-aminomethyl-4,5-didehydro-19(R)-19-hydroxy-11-deoxy-15(S)-15-methyl-PGE$_1$,
2-decarboxy-2-aminomethyl-4,5,13,14-tetradehydro-19(R)-19-hydroxy-11-deoxy-PGE$_1$,
2-decarboxy-2-aminomethyl-4,5,13,14-tetradehydro-19(R)-19-hydroxy-11-deoxy-16,16-difluoro-PGE$_1$,
2-decarboxy-2-aminomethyl-4,5-didehydro-19(R)-19-hydroxy-11-deoxy-11α-hydroxymethyl-PGE$_1$,
2-decarboxy-2-aminomethyl-4,5-didehydro-19(R)-19-hydroxy-11-deoxy-11α-hydroxymethyl-15(S)-15-methyl-PGE$_1$,
2-decarboxy-2-aminomethyl-4,5,13,14-tetradehydro-19-(R)-19-hydroxy-11-deoxy-11α-hydroxymethyl-PGE$_1$,
2-decarboxy-2-aminomethyl-4,5,13,14-tetradehydro-19(R)-19-hydroxy-11-deoxy-11α-hydroxymethyl-16,16-difluoro-PGE$_1$,
2-Decarboxy-2-aminomethyl-4,5-didehydro-19(R)-19-hydroxy-9-deoxo-9-methylene-PGE$_1$,
2-Decarboxy-2-aminomethyl-4,5-didehydro-19(R)-19-hydroxy-9-deoxo-9-methylene-15(S)-15-methyl-PGE$_1$,
2-decarboxy-2-aminomethyl-4,5,13,14-tetradehydro-19(R)-19-hydroxy-9-deoxo-9-methylene-PGE$_1$,
2-decarboxy-2-aminomethyl-4,5,13,14-tetradehydro19(R)-19-hydroxy-9-deoxo-9-methylene-16,16-difluoro-PGE$_1$,
2-decarboxy-2-aminomethyl-4,5-didehydro-19(R)-19-hydroxy-9-deoxo-9-methylene-11-deoxy-PGE$_1$,
2-decarboxy-2-aminomethyl-4,5-didehydro-19(R)-19-hydroxy-9-deoxo-9-methylene-15(S)-15-methyl-PGE$_1$,
2-decarboxy-2-aminomethyl-4,5,13,14-tetradehydro-19(R)-19-hydroxy-9-deoxo-9-methylene-11-deoxy-PGE$_1$,
2-decarboxy-2-aminomethyl-4,5,13,14-tetradehydro-19(R)-19-hydroxy-9-deoxo-9-methylene-11-deoxy-16,16-difluoro-PGE$_1$,
2-decarboxy-2-aminomethyl-4,5-didehydro-19(R)-19-hydroxy-9-deoxo-9-methylene-11-deoxy-11α-hydroxymethyl-PGE$_1$,
2-decarboxy-2-aminomethyl-4,5-didehydro-19(R)-19-hydroxy-9-deoxo-9-methylene-11-deoxy-11α-hydroxymethyl15-(S)-15-methyl-PGE$_1$,
2-decarboxy-2-aminomethyl-4,5,13,14-tetradehydro-19(R)-19-hydroxy-9-deoxo-9-methylene-11-deoxy-11α-hydroxy-methyl-PGE$_1$,
2-decarboxy-2-aminomethyl-4,5,13,14-tetradehydro-19(R)-19-hydroxy-9-deoxo-9-methylene-11-deoxy-11α-hydroxymethyl-16,-difluoro-PGE$_1$,
2-decarboxy-2-aminomethyl-2,3-didehydro-19(R)-19-hydroxy-PGF$_{1\alpha}$,
2-decarboxy-2-aminomethyl-2,3-didehydro-19(R)-19-hydroxy-16,16-difluoro-PGF$_{1\alpha}$,
2-decarboxy-2-aminomethyl-2,3-didehydro-19(R)-19-hydroxy-15(S)-15-methyl-PGF$_{1\alpha}$,
2-decarboxy-2-aminomethyl-2,3-didehydro-19(R)-19-hydroxy-11-deoxy-PGF$_{1\alpha}$,
2-decarboxy-2-aminomethyl-2,3-didehydro-19(R)-19-hydroxy-11-deoxy-16,16-difluoro-PGF$_{1\alpha}$,
2-decarboxy-2-aminomethyl-2,3-didehydro-19(R)-19-hydroxy-11-deoxy-15(S)-15-methyl-PGF$_{1\alpha}$,
2-decarboxy-2-aminomethyl-2,3-didehydro-19(R)-19-hydroxy-11-deoxy-11α-hydroxymethyl-PGF$_{1\alpha}$,
2-decarboxy-2-aminomethyl-2,3-didehydro-19(R)-19-hydroxy-11-deoxy-11α-hydroxymethyl-16,16-difluoro-PGF$_{1\alpha}$,
2-decarboxy-2-aminomethyl-2,3-didehydro-19(R)-19-hydroxy-11-deoxy-11α-hydroxymethyl-15(S)-15-methyl-PGF$_{1\alpha}$,
2-decarboxy-2-aminomethyl-2,3-didehydro-19(R)-19-hydroxy-PGF$_{1\beta}$,
2-decarboxy-2-aminomethyl-2,3-didehydro-19(R)-19-hydroxy-16,16-difluoro-PGF$_{1\beta}$,
2-decarboxy-2-aminomethyl-2,3-didehydro-19(R)-19-hydroxy-15(S)-methyl-PGF$_{1\beta}$,
2-decarboxy-2-aminomethyl-2,3-didehydro-19(R)-19-hydroxy-11-deoxy-PGF$_{1\beta}$,
2-decarboxy-2-aminomethyl-2,3-didehydro-19(R)-19-hydroxy-11-deoxy-16,16-difluoro-PGF$_{1\beta}$,
2-decarboxy-2-aminomethyl-2,3-didehydro-19(R)-19-hydroxy-11-deoxy-15(S)-methyl-PGF$_{1\beta}$,
2-decarboxy-2-aminomethyl-2,3-didehydro-19(R)-19-hydroxy-11-deoxy-11α-hydroxymethyl-PGF$_{1\beta}$,
2-decarboxy-2-aminomethyl-2,3-didehydro-19(R)-19-hydroxy-11-deoxy-11α-hydroxymethyl-16,16-difluoro-PGF$_{1\beta}$,
2-decarboxy-2-aminomethyl-2,3-didehydro-19(R)-19-hydroxy-11-deoxy-11α-hydroxymethyl-15(S)-15-methyl-PGF$_{1\beta}$,
2-decarboxy-2-aminomethyl-2,3-didehydro-19(R)-19-hydroxy-PGE$_1$,
2-decarboxy-2-aminomethyl-2,3-didehydro-19(R)-19-hydroxy-16,16-difluoro-PGE$_1$,
2-decarboxy-2-aminomethyl-2,3-didehydro-19(R)-19-hydroxy-15(S)-15-methyl-PGE$_1$,
2-decarboxy-2-aminomethyl-2,3-didehydro-19(R)-19-hydroxy-11-deoxy-PGE$_1$,
2-decarboxy-2-aminomethyl-2,3-didehydro-19(R)-19-hydroxy-11-deoxy-16,16-difluoro-PGE$_1$,
2-decarboxy-2-aminomethyl-2,3-didehydro-19(R)-19-hydroxy-11-deoxy-15(S)-15-methyl-PGE$_1$,
2-decarboxy-2-aminomethyl-2,3-didehydro-19(R)-19-hydroxy-11-deoxy-11α-hydroxymethyl-PGE$_1$, 2-decarboxy-2-aminomethyl-2,3-didehydro-19(R)-19-hydroxy-11-deoxy-11α-hydroxymethyl-16,16-difluoro-PGE₁,
2-decarboxy-2-aminomethyl-2,3-didehydro-19(R)-19-hydroxy-11-deoxy-11α-hydroxymethyl-15(S)-15-methyl-PGE₁,
2-decarboxy-2-aminomethyl-2,3-didehydro-19(R)-19-hydroxy-9-deoxo-9-methylene-PGE₁,
2-decarboxy-2-aminomethyl-2,3-didehydro-19(R)-19-hydroxy-9-deoxo-9-methylene-16,16-difluoro-PGE₁,
2-decarboxy-2-aminomethyl-2,3-didehydro-19(R)-19-hydroxy-9-deoxo-9-methylene-15(S)-15-methyl-PGE₁,
2-decarboxy-2-aminomethyl-2,3-didehydro-19(R)-19-hydroxy-9-deoxo-9-methylene-11-deoxy-PGE₁,
2-decarboxy-2-aminomethyl-2,3-didehydro-19(R)-19-hydroxy-9-deoxo-9-methylene-11-deoxy-16,16-difluoro-PGE₁,
2-decarboxy-2-aminomethyl-2,3-didehydro-19(R)-19-hydroxy-9-deoxo-9-methylene-11-deoxy-15(S)-15-methyl PGE₁,
2-decarboxy-2-aminomethyl-19(R)-19-hydroxyPGF$_{1α}$,
2-decarboxy-2-aminomethyl-16,16-dimethyl-19(R)-19-hydroxy-PGFxzl,
2-Decarboxy-2-aminomethyl-16,16-difluoro-19(R)-19-hydroxy-PGF$_{1α}$,
2-decarboxy-2-aminomethyl-13,14-dihydro-19(R)-19-hydroxy-PGF$_{1α}$,
2-decarboxy-2-aminomethyl-11-deoxy-19(R)-19-hydroxy-PGF$_{1α}$,
2-decarboxy-2-aminomethyl-11-deoxy-16,16-dimethyl-19(R)-19-hydroxy-PGF$_{1α}$,
2-decarboxy-2-aminomethyl-11-deoxy-16,16-difluoro-19(R)-19-hydroxy-PGF$_{1α}$,
2-decarboxy-2-aminomethyl-11-deoxy-13,14-dihydro-19(R)-19-hydroxy-PGF$_{1α}$,
2-decarboxy-2-aminomethyl-11-deoxy-11α-hydroxymethyl-19(R)-19-hydroxy-PGF$_{1α}$,
2-decarboxy-2-aminomethyl-11-deoxy-11α-hydroxymethyl-16,16-dimethyl-19(R)-19-hydroxy-PGF$_{1α}$,
2-decarboxy-2-aminomethyl-11-deoxy-11α-hydroxymethyl-16,16-difluoro-19(R)-19-hydroxy-PGF$_{1α}$,
2-decarboxy-2-aminomethyl-11-deoxy-11α-hydroxymethyl-13,14-dihydro-19(R)-19-hydroxy-PGF$_{1α}$,
2-decarboxy-2-aminomethyl-19(R)-19-hydroxy-PGF$_{1β}$,
2-decarboxy-2-aminomethyl-16,16-dimethyl-19(R)-19-hydroxy-PGF$_{1β}$,
2-decarboxy-2-aminomethyl-16,16-difluoro-19(R)-19-hydroxy-PGF$_{1β}$,
2-decarboxy-2-aminomethyl-13,14-dihydro-19(R)-19-hydroxy-PGF$_{2β}$,
2-decarboxy-2-aminomethyl-11-deoxy-19(R)-19-hydroxy-PGF$_{1β}$,
2-decarboxy-2-aminomethyl-11-deoxy-16,16-dimethyl-19(R)-19-hydroxy-PGF$_{1β}$,
2-decarboxy-2-aminomethyl-16,16-difluoro-19(R)-19 hydroxy-PGF$_{1β}$,
2-decarboxy-2-aminomethyl-11-deoxy-13,14-dihydro-19(R)-19-hydroxy-PGF$_{1β}$,
2-decarboxy-2-aminomethyl-11-deoxy-11α-hydroxymethyl-19(R)-19-hydroxy-PGF$_{1β}$,
2-decarboxy-2-aminomethyl-11-deoxy-11α-hydroxymethyl-16,16-dimethyl-19(R)-19-hydroxy-PGF$_{1β}$,
2-decarboxy-2-aminomethyl-11-deoxy-11α-hydroxymethyl-16,16-difluoro-19(R)-19-hydroxy-PGF$_{1β}$,
2-decarboxy-2-aminomethyl-11-deoxy-11α-hydroxymethyl-13,14-dihydro-19(R)-19-hydroxy-PGF$_{1β}$,
2-decarboxy-2-aminomethyl-19(R)-19-hydroxy-PGE₁,
2-decarboxy-2-aminomethyl-16,16-dimethyl-19(R)-19-hydroxy-PGE₁,
2-decarboxy-2-aminomethyl-16,16-difluoro-19(R)-19-hydroxy-PGE₁,
2-decarboxy-2-aminomethyl-13,14-dihydro-19(R)-19-hydroxy-PGE₁,
2-decarboxy-2-aminomethyl-11-deoxy-19(R)-19-hydroxy-PGE₁,
2-decarboxy-2-aminomethyl-11-deoxy-16,16-dimethyl-19(R)-19-hydroxy-PGE₁,
2-decarboxy-2-aminomethyl-11-deoxy-16,16-difluoro-19(R)-19-hydroxy-PGE₁,
2-decarboxy-2-aminomethyl-11-deoxy-13,14-dihydro-19(R)-19-hydroxy-PGE₁,
2-decarboxy-2-aminomethyl-11-deoxy-11α-hydroxymethyl-19(R)-19-hydroxy-PGE₁,
2-decarboxy-2-aminomethyl-11-deoxy-11α-hydroxymethyl-16,16-dimethyl-19(R)-19-hydroxy-PGE₁,
2-decarboxy-2-aminomethyl-11-deoxy-11α-hydroxymethyl-16,16-difluoro-19(R)-19-hydroxy-PGE₁,
2-decarboxy-2-aminomethyl-11-deoxy-11α-hydroxymethyl-13,14-dihydro-19(R)-19-hydroxy-PGE₁,
2-decarboxy-2-aminomethyl-9-deoxo-9-methylene-19(R)-19-hydroxy-PGE₁,
2-decarboxy-2-aminomethyl-9-deoxo-9-methylene-16,16-dimethyl-19(R)-19-hydroxy-PGE₁,
2-decarboxy-2-aminomethyl-9-deoxo-9-methylene-16,16-difluoro-19(R)-19-hydroxy-PGE₁,
2-decarboxy-2-aminomethyl-9-deoxo-9-methylene-13,14dihydro-19(R)-19-hydroxy-PGE₁,
2-decarboxy-2-aminomethyl-9-deoxo-9-methylene-11-deoxy-19(R)-19-hydroxy-PGE₁,
2-decarboxy-2-aminomethyl-9-deoxo-9-methylene-11-deoxy-16,16-dimethyl-19(R)-19-hydroxy-PGE₁,
2-Decarboxy-2-aminomethyl-9-deoxo-9-methylene-1-deoxy-16,16-difluoro-19(R)-19-hydroxy-PGE₁,
2-decarboxy-2-aminomethyl-9-deoxo-9-methylene-11-deoxy-13,14-dihydro-19(R)-19-hydroxy-PGE₁,
2-decarboxy-2-aminomethyl-9-deoxo-9-methylene-11-deoxy-11α-hydroxymethyl-19(R)-19-hydroxy-PGE₁,
2-decarboxy-2-aminomethyl-9-deoxo-9-methylene-11-deoxy-11α-hydroxymethyl-16,16-dimethyl-19(R)-19-hydroxy-PGE₁,
2-decarboxy-2-aminomethyl-9-deoxo-9-methylene-11-deoxy-11α-hydroxymethyl-16,16-difluoro-19(R)-19-hydroxy-PGE₁,
2-decarboxy-2-aminomethyl-9-deoxo-9-methylene-11-deoxy-11α-hydroxymethyl-13,14-dihydro-19(R)-19-hydroxy-PGE₁, The compounds of the present invention are particularly useful for inducing prostaglandin-like biological effects, as is described in U.S. Ser. No. 025,899. Uses of compounds in accordance with the present invention include, therefore, anti-asthmatic indications.

I claim:

1. A compound of the formula

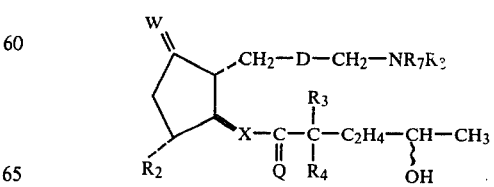

wherein D is (1) cis-CH=CH—CH₂—(CH₂)$_g$—CH₂—, (2) cis-CH=CH—CH$_2$—(CH$_2$)$_g$—CF$_2$—,
(3) cis-CH$_2$—CH=CH—CH$_2$—CH$_2$—,
(4) trans-(CH$_2$)$_3$—CH=CH—,
(5) —(CH$_2$)$_3$—(CH$_2$)$_g$—CH$_2$—,
(6) —(CH$_2$)$_3$—CH$_2$—CF$_2$—,
(7) —(CH$_2$)$_3$—O—CH$_2$—,
(8) —(CH$_2$)$_2$—O—(CH$_2$)$_2$—,
(9) —CH$_2$—O—(CH$_2$)$_3$—,
(10) —(m-ph)—(CH$_2$)$_2$—, or
(11) —(m-ph)—O—CH$_2$—
wherein m-ph is inter-meta-phenylene, and
wherein g is zero, one, two, or three;
wherein Q is α-OH:β-R$_5$ or α-R$_5$:β-OH,
wherein R$_5$ is hydrogen or methyl,
wherein R$_7$ and R$_8$ are hydrogen, alkyl of one to 12 carbon atoms, inclusive, benzyl, or phenyl, being the same or different;
wherein R$_2$ is hydrogen, hydroxyl, or hydroxymethyl;
wherein R$_3$ and R$_4$ are hydrogen, methyl, or fluoro, being the same or different, with the proviso that one of R$_3$ and R$_4$ is fluoro only when the other is hydrogen or fluoro;
wherein W is oxo, methylene, α-OH:B-H, or α-H:β-OH;
and wherein X is cis- or trans-CH=CH—, —C≡C—, or —CH$_2$CH$_2$—.

2. A compound according to claim 1 wherein g is one or three.

3. A compound according to claim 2, wherein D is cis-CH=CH—CH$_2$—(CH$_2$)$_g$—CH$_2$—.

4. A compound according to claim 3, wherein W is

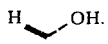

5. A compound according to claim 4, wherein R$_2$ is hydroxyl and X is trans-CH=CH—.

6. 2-Decarboxy-2-aminomethyl-19(R)-19-hydroxyPGF$_{2\alpha}$, a compound according to claim 5.

7. A compound according to claim 4, wherein R$_2$ is hydrogen and X is trans-CH=CH—.

8. 2-Decarboxy-2-aminomethyl-11-deoxy-19(R)-19-hydroxy-PGF$_{2\alpha}$, a compound according to claim 7.

9. A compound according to claim 4, wherein R$_2$ is hydroxymethyl and X is trans-CH=CH—.

10. 2-Decarboxy-2-aminomethyl-11-deoxy-11α-hydroxymethyl-19(R)-19-hydroxy-PGF$_{2\alpha}$, a compound according to claim 9.

11. A compound according to claim 3, wherein W is

12. A compound according to claim 11, wherein R$_2$ is hydroxyl and X is trans-CH=CH—.

13. 2-Decarboxy-2-aminomethyl-19(R)-19-hydroxy-PGF$_{2\beta}$, a compound according to claim 12.

14. A compound according to claim 11, wherein R$_2$ is hydrogen and X is trans-CH=CH—.

15. 2-Decarboxy-2-aminomethyl-11-deoxy-19(R)-hydroxy-PGF$_{2\beta}$, a compound according to claim 14.

16. A compound according to claim 11, wherein R$_2$ is hydroxymethyl and X is trans-CH=CH—.

17. 2-Decarboxy-2-aminomethyl-11-deoxy-11α-hydroxymethyl-19(R)-19-hydroxy-PGF$_{2\beta}$, a compound according to claim 16.

18. A compound according to claim 3, wherein W is

19. A compound according to claim 18, wherein R$_2$ is hydroxyl and X is trans-CH=CH—.

20. 2-Decarboxy-2-aminomethyl-19(R)-19-hydroxy-PGE$_2$, a compound according to claim 19.

21. A compound according to claim 19, wherein R$_2$ is hydrogen and X is trans-CH=CH—.

22. 2-Decarboxy-2-aminomethyl-11-deoxy-19(R)-19-hydroxy-PGE$_2$, a compound according to claim 21.

23. A compound according to claim 18, wherein R$_2$ is hydroxymethyl and X is trans-CH=CH—.

24. 2-Decarboxy-2-aminomethyl-11-deoxy-11α-hydroxy methyl-19(R)-19-hydroxy-PGE$_2$, a compound according to claim 23.

25. A compound according to claim 3, wherein W is

26. A compound according to claim 25, wherein R$_2$ is hydroxyl and X is trans-CH=CH—.

27. 2-Decarboxy-2-aminomethyl-9-deoxo-9-methylene-19(R)-19-hydroxy-PGE$_2$, a compound according to claim 26.

28. A compound according to claim 25, wherein R$_2$ is hydrogen and X is trans-CH=CH—.

29. 2-Decarboxy-2-aminomethyl-9-deoxo-9-methylene-11-deoxy-19(R)-19-hydroxy-PGE$_2$, a compound according to claim 28.

30. A compound according to claim 25, wherein R$_2$ is hydroxymethyl and X is trans-CH=CH—.

31. 2-Decarboxy-2-aminomethyl-9-deoxo-9-methylene-11-deoxy-11α-hydroxymethyl-19(R)-19-hydroxy-PGE$_2$, a compound according to claim 30.

32. A compound according to claim 2, wherein D is cis-CH$_2$—CH=CH—CH$_2$—CH$_2$—.

33. A compound according to claim 32, wherein W is

34. A compound according to claim 33, wherein R$_2$ is hydroxyl.

35. A compound according to claim 34, wherein X is trans-CH=CH—.

36. 2-Decarboxy-2-aminomethyl-4,5-didehydro-19(R)-19-hydroxy-PGF$_{1\alpha}$, a compound according to claim 35.

37. 2-Decarboxy-2-aminomethyl-4,5-didehydro-19(R)-19-hydroxy-15(S)-15-methyl-PGF$_{1\alpha}$, a compound according to claim 35.

38. A compound according to claim 34, wherein X is —C≡C—.

39. 2-Decarboxy-2-aminomethyl-4,5,13,14,-tetradehydro-19(R)-19-hydroxy-PGF$_{1\alpha}$, a compound according to claim 38.

40. 2-Decarboxy-2-aminomethyl-4,5,13,14-tetradehydro-19(R)-19-hydroxy-16,16-difluoro-PGF$_{1\alpha}$, a compound according to claim 38.

41. A compound according to claim 33, wherein $R_2$ is hydrogen.

42. A compound according to claim 41, wherein X is trans-CH=CH—.

43. 2-Decarboxy-2-aminomethyl-4,5-didehydro-19(R)-19-hydroxy-11-deoxy-PGF$_{1\alpha}$, a compound according to claim 42.

44. 2-Decarboxy-2-aminomethyl-4,5-didehydro-19(R)-19-hydroxy-11-deoxy-15(S)-15-methyl-PGF$_{1\alpha}$, a compound according to claim 42.

45. A compound according to claim 41, wherein X is —C≡C—.

46. 2-Decarboxy-2-aminomethyl-4,5,13,14-tetradehydro-19(R)-19-hydroxy-11-deoxy-PGF$_{1\alpha}$, a compound according to claim 45.

47. 2-Decarboxy-2-aminomethyl-4,5,13,14-tetradehydro-19(R)-19-hydroxy-11-deoxy-16,16-difluoro-PGF$_{1\alpha}$, a compound according to claim 45.

48. A compound according to claim 33, wherein $R_2$ is hydroxymethyl.

49. A compound according to claim 48, wherein X is trans-CH=CH—.

50. 2-Decarboxy-2-aminomethyl-4,5-didehydro-19(R)-19-hydroxy-11-deoxy-11α-hydroxymethyl-PGF$_{1\alpha}$, a compound according to claim 49.

51. 2-Decarboxy-2-aminomethyl-4,5-didehydro-19(R)-19-hydroxy-11-deoxy-11α-hydroxymethyl-15(S)-15-methyl-PGF$_{1\alpha}$, a compound according to claim 49.

52. A compound according to claim 48, wherein X is —C≡C—.

53. 2-Decarboxy-2-aminomethyl-4,5,13,14-tetradehydro-19(R)-19-hydroxy-11-deoxy-11α-hydroxymethyl-PGF$_{1\alpha}$, a compound according to claim 52.

54. 2-Decarboxy-2-aminomethyl-4,5,13,14-tetradehydro-19(R)-19-hydroxy-11-deoxy-11α-hydroxymethyl-16,16-difluoro-PGF$_{1\alpha}$, a compound according to claim 52.

55. A compound according to claim 32, wherein W is

56. A compound according to claim 55, wherein $R_2$ is hydroxyl.

57. A compound according to claim 56, wherein X is trans-CH=CH—.

58. 2-Decarboxy-2-aminomethyl-4,5-didehydro-19(R)-19-hydroxy-PGF$_{1\beta}$, a compound according to claim 57.

59. 2-Decarboxy-2-aminomethyl-4,5-didehydro-19(R)-19-hydroxy-15(S)-15-methyl-PGF$_{1\beta}$, a compound according to claim 57.

60. A compound according to claim 56, wherein X is —C≡C—.

61. 2-Decarboxy-2-aminomethyl-4,5,13,14-tetradehydro-19(R)-19-hydroxy-PGF$_{1\beta}$, a compound according to claim 60.

62. 2-Decarboxy-2-aminomethyl-4,5,13,14-tetradehydro-19(R)-19-hydroxy-16,16-difluoro-PGF$_{1\beta}$, a compound according to claim 60.

63. A compound according to claim 55, wherein $R_2$ is hydrogen.

64. A compound according to claim 63, wherein X is trans—CH=CH—.

65. 2-Decarboxy-2-aminomethyl-4,5-didehydro-19(R)-19-hydroxy-11-deoxy-PGF$_{1\beta}$, a compound according to claim 64.

66. 2-Decarboxy-2-aminomethyl-4,5-didehydro-19(R)-19-hydroxy-11-deoxy-15(S)-15-methyl-PGF$_{1\beta}$, a compound according to claim 64.

67. A compound according to claim 63, wherein X is —C≡C—.

68. 2-Decarboxy-2-aminomethyl-4,5,13,14-tetradehydro-19(R)-19-hydroxy-11-deoxy-PGF$_{1\beta}$, a compound according to claim 67.

69. 2-Decarboxy-2-aminomethyl-4,5,13,14-tetradehydro-19(R)-19-hydroxy-11-deoxy-16,16-difluoro-PGF$_{1\beta}$, a compound according to claim 67.

70. A compound according to claim 55, wherein $R_2$ is hydroxymethyl.

71. A compound according to claim 70, wherein X is trans-CH=CH—.

72. 2-Decarboxy-2-aminomethyl-4,5-didehydro-19(R)-19-hydroxy-11-deoxy-11α-hydroxymethyl-PGF$_{1\beta}$, a compound according to claim 71.

73. 2-Decarboxy-2-aminomethyl-4,5-didehydro-19(R)-19-hydroxy-11-deoxy-11α-hydroxymethyl-15(S)-15-methyl-PGF$_{1\beta}$, a compound according to claim 71.

74. A compound according to claim 70, wherein X is —C≡C—.

75. 2-Decarboxy-2-aminomethyl-4,5,13,14-tetradehydro-19(R)-19-hydroxy-11-deoxy-11α-hydroxymethyl-PGF$_{1\beta}$, a compound according to claim 74.

76. 2-Decarboxy-2-aminomethyl-4,5,13,14-tetradehydro-19(R)-19-hydroxy-11-deoxy-11α, hydroxymethyl-16,16-difluoro-PGF$_{1\beta}$, a compound according to claim 74.

77. A compound according to claim 32, wherein W is

78. A compound according to claim 77, wherein $R_2$ is hydroxyl.

79. A compound according to claim 78, wherein X is trans-CH=CH—.

80. 2-Decarboxy-2-aminomethyl-4,5-didehydro-19(R)-19-hydroxy-PGE$_1$, a compound according to claim 79.

81. 2-Decarboxy-2-aminomethyl-4,5-didehydro-19(R)-19-hydroxy-15(S)-15-methyl-PGE$_1$, a compound according to claim 79.

82. A compound according to claim 78, wherein X is —C≡C—.

83. 2-Decarboxy-2-aminomethyl-4,5,13,14-tetradehydro-19(R)-19-hydroxy-PGE$_1$, a compound according to claim 82.

84. 2-Decarboxy-2-aminomethyl-4,5,13,14-tetradehydro-19(R)-19-hydroxy-16,16-difluoro-PGE$_1$, a compound according to claim 82.

85. A compound according to claim 77, wherein $R_2$ is hydrogen.

86. A compound according to claim 85, wherein X is trans-CH=CH—.

87. 2-Decarboxy-2-aminomethyl-4,5-didehydro-19(R)-19-hydroxy-11-deoxy-PGE$_1$, a compound according to claim 86.

88. 2-Decarboxy-2-aminomethyl-4,5-didehydro-19(R)-19-hydroxy-11-deoxy-15(S)-15-methyl-PGE$_1$, a compound according to claim 86.

89. A compound according to claim 85, wherein X is —C≡C—.

90. 2-Decarboxy-2-aminomethyl-4,5,13,14-tetradehydro-19(R)-19-hydroxy-11-deoxy-PGE₁, a compound according to claim 89.

91. 2-Decarboxy-2-aminomethyl-4,5,13,14-tetradehydro-19(R)-19-hydroxy-11-deoxy-16,16-difluoro-PGE₁, a compound according to claim 89.

92. A compound according to claim 77, wherein R₂ is hydroxymethyl.

93. A compound according to claim 92, wherein X is trans-CH=CH—.

94. 2-Decarboxy-2-aminomethyl-4,5-didehydro-19(R)-19-hydroxy-11-deoxy-11α-hydroxymethyl-PGE₁, a compound according to claim 93.

95. 2-Decarboxy-2-aminomethyl-4,5-didehydro-19(R)-19-hydroxy-11-deoxy-11α-hydroxymethyl-15(S)-15-methyl-PGE₁, a compound according to claim 93.

96. A compound according to claim 92, wherein X is —C≡C—.

97. 2-Decarboxy-2-aminomethyl-4,5,13,14-tetradehydro-19(R)-19-hydroxy-11-deoxy-11α-hydroxymethyl-PGE₁, a compound according to claim 96.

98. 2-Decarboxy-2-aminomethyl-4,5,13,14-tetradehydro 19(R)-19-hydroxy-11-deoxy-11α-hydroxymethyl-16,16-difluoro-PGE₁, a compound according to claim 96.

99. A compound according to claim 32, wherein W is

100. A compound according to claim 99, wherein R₂ is hydroxyl.

101. A compound according to claim 100, wherein X is trans-CH=CH—.

102. 2-Decarboxy-2-aminomethyl-4,5-didehydro-19(R)-19-hydroxy-9-deoxo-9-methylene-PGE₁, a compound according to claim 101.

103. 2-Decarboxy-2-aminomethyl-4,5-didehydro-19(R)-19-hydroxy-9-deoxo-9-methylene-15(S)-15-methyl-PGE₁, a compound according to claim 101.

104. A compound according to claim 100, wherein X is —C≡C—.

105. 2-Decarboxy-2-aminomethyl-4,5,13,14-tetradehydro-19(R)-19-hydroxy-9-deoxo-9-methylene-PGE₁, a compound according to claim 104.

106. 2-Decarboxy-2-aminomethyl-4,5,13,14-tetradehydro19(R)-19-hydroxy-9-deoxo-9-methylene-16,16-difluoro-PGE₁, a compound according to claim 105.

107. A compound according to claim 99, wherein R₂ is hydrogen.

108. A compound according to claim 107, wherein X is trans-CH=CH—.

109. 2-Decarboxy-2-aminomethyl-4,5-didehydro-19(R)-19-hydroxy-9-deoxo-9-methylene-11-deoxy-PGE₁, a compound according to claim 108.

110. 2-Decarboxy-2-aminomethyl-4,5-didehydro-19(R)-19-hydroxy-9-deoxo-9-methylene-15(S)-15-methyl-PGE₁, a compound according to claim 108.

111. A compound according to claim 107, wherein X is —C≡C—.

112. 2-Decarboxy-2-aminomethyl-4,5,13,14-tetradehydro-19(R)-19-hydroxy-9-deoxo-9-methylene-11-deoxy-PGE₁, a compound according to claim 111.

113. 2-Decarboxy-2-aminomethyl-4,5,13,14-tetradehydro-19(R)-19-hydroxy-9-deoxo-9-methylene-11-deoxy-16,16-difluoro-PGE₁, a compound according to claim 111.

114. A compound according to claim 99, wherein R₂ is hydroxymethyl.

115. A compound according to claim 114, wherein X is trans-CH=CH—.

116. 2-Decarboxy-2-aminomethyl-4,5-didehydro-19(R)-19-hydroxy-9-deoxo-9-methylene-11-deoxy-11α-hydroxymethyl-PGE₁, a compound according to claim 115.

117. 2-Decarboxy-2-aminomethyl-4,5-didehydro-19(R)-19-hydroxy-9-deoxo-9-methylene-11-deoxy-11α-hydroxymethyl-15-(S)-15-methyl-PGE₁, a compound according to claim 115.

118. A compound according to claim 114, wherein X is —C≡C—.

119. 2-Decarboxy-2-aminomethyl-4,5,13,14-tetradehydro-19(R)-19-hydroxy-9-deoxo-9-methylene-11-deoxy-11α-hydroxy-methyl-PGE₁, a compound according to claim 118.

120. 2-Decarboxy-2-aminomethyl-4,5,13,14-tetradehydro-19(R)-19-hydroxy-9-deoxo-9-methylene-11-deoxy-11α-hydroxymethyl-16,-16-difluoro-PGE₁, a compound according to claim 118.

121. A compound according to claim 2, wherein D is trans-(CH₂)₃—CH=CH—.

122. A compound according to claim 121, wherein W is

123. A compound according to claim 122, wherein R₂ is hydroxyl and X is trans-CH=CH—.

124. 2-Decarboxy-2-aminomethyl-2,3-didehydro-19(R)-19-hydroxy-PGF₁α, a compound according to claim 123.

125. 2-Decarboxy-2-aminomethyl-2,3-didehydro-19(R)-19-hydroxy-16,16-difluoro-PGF₁α, a compound according to claim 123.

126. 2-Decarboxy-2-aminomethyl-2,3-didehydro-19(R)-19-hydroxy-15(S)-15-methyl-PGF₁α, a compound according to claim 123.

127. A compound according to claim 122, wherein R₂ is hydrogen and X is trans-CH=CH—.

128. 2-Decarboxy-2-aminomethyl-2,3-didehydro-19(R)-19-hydroxy-11-deoxy-PGF₁α, a compound according to claim 127.

129. 2-Decarboxy-2-aminomethyl-2,3-didehydro-19(R)-19-hydroxy-11-deoxy-16,16-difluoro-PGF₁α, a compound according to claim 127.

130. 2-Decarboxy-2-aminomethyl-2,3-didehydro-19(R)-19-hydroxy-11-deoxy-15(S)-15-methyl-PGF₁α, a compound according to claim 127.

131. A compound according to claim 122, wherein R₂ is hydroxymethyl, and X is trans-CH=CH—.

132. 2-Decarboxy-2-aminomethyl-2,3-didehydro-19(R)-19-hydroxy-11-deoxy-11α-hydroxymethyl-PGF₁α, a compound according to claim 131.

133. 2-Decarboxy-2-aminomethyl-2,3-didehydro-19(R)-19-hydroxy-11-deoxy-11α-hydroxymethyl-16,16-difluoro-PGF₁α, a compound according to claim 131.

134. 2-Decarboxy-2-aminomethyl-2,3-didehydro-19(R)-19-hydroxy-11-deoxy-11α-hydroxymethyl-15(S)-15-methyl-PGF₁α, a compound according to claim 131.

135. A compound according to claim 121, wherein W is

136. A compound according to claim 135, wherein R₂ is hydroxyl and X is trans-CH=CH—.

137. 2-Decarboxy-2-aminomethyl-2,3-didehydro-19(R)-19-hydroxy-PGF₁β, a compound according to claim 136.

138. 2-Decarboxy-2-aminomethyl-2,3-didehydro-19(R)-19-hydroxy-16,16-difluoro-PGF₁β, a compund according to claim 136.

139. 2-Decarboxy-2-aminomethyl-2,3-didehydro-19(R)-19-hydroxy-15(S)-methyl-PGF₁β, a compound according to claim 136.

140. A compound according to claim 135, wherein R₂ is hydrogen and X is trans-CH=CH—.

141. 2-Decarboxy-2-aminomethyl-2,3-didehydro-19(R)-19-hydroxy-11-deoxy-PGF₁β, a compound according to claim 140.

142. 2-Decarboxy-2-aminomethyl-2,3-didehydro-19(R)-19-hydroxy-11-deoxy-16,16-difluoro-PGF₁β, a compound according to claim 140.

143. 2-Decarboxy-2-aminomethyl-2,3-didehydro-19(R)-19-hydroxy-11-deoxy-15(S)-15-methyl-PGF₁β, a compound according to claim 140.

144. A compound according to claim 135, wherein R₂ is hydroxymethyl, and X is trans-CH=CH—.

145. 2-Decarboxy-2-aminomethyl-2,3-didehydro-19(R)-19-hydroxy-11-deoxy-11α-hydroxymethyl-PGF₁β, a compound according to claim 144.

146. 2-Decarboxy-2-aminomethyl-2,3-didehydro-19(R)-19-hydroxy-11-deoxy-11α-hydroxymethyl-16,16-difluoro-PGF₁β, a compound according to claim 144.

147. 2-Decarboxy-2-aminomethyl-2,3-didehydro-19(R)-19-hydroxy-11-deoxy-11α-hydroxymethyl-15(S)-15-methyl-PGF₁β, a compound according to claim 144.

148. A compound according to claim 121, wherein W is

149. A compound according to claim 148, wherein R₂ is hydroxyl and X is trans-CH=CH—.

150. 2-Decarboxy-2-aminomethyl-2,3-didehydro-19(R)-19-hydroxy-PGE₁, a compound according to claim 149.

151. 2-Decarboxy-2-aminomethyl-2,3-didehydro-19(R)-19-hydroxy-16,16-difluoro-PGE₁, a compound according to claim 149.

152. 2-Decarboxy-2-aminomethyl-2,3-didehydro-19(R)-19-hydroxy-15(S)-15-methyl-PGE₁, a compound according to claim 149.

153. A compound according to claim 148, wherein R₂ is hydrogen and X is trans-CH=CH—.

154. 2-Decarboxy-2-aminomethyl-2,3-didehydro-19(R)-19-hydroxy-11-deoxy-PGE₁, a compound according to claim 153.

155. 2-Decarboxy-2-aminomethyl-2,3-didehydro-19(R)-19-hydroxy-11-deoxy-16,16-difluoro-PGE₁, a compound according to claim 153.

156. 2-Decarboxy-2-aminomethyl-2,3-didehydro-19(R)-19-hydroxy-11-deoxy-15(S)-15-methyl-PGE₁, a compound according to claim 153.

157. A compound according to claim 148, wherein R₂ is hydroxymethyl, and X is trans-CH=CH—.

158. 2-Decarboxy-2-aminomethyl-2,3-didehydro-19(R)-19-hydroxy-11-deoxy-11α-hydroxymethyl-PGE₁, a compound according to claim 157.

159. 2-Decarboxy-2-aminomethyl-2,3-didehydro-19(R)-19-hydroxy-11-deoxy-11α-hydroxymethyl-16,16-difluoro-PGE₁, a compound according to claim 157.

160. 2-Decarboxy-2-aminomethyl-2,3-didehydro-19(R)-19-hydroxy-11-deoxy-11α-hydroxymethyl-15(S)-15-methyl-PGE₁, a compound according to claim 157.

161. A compound according to claim 121, wherein W is

162. A compound according to claim 161, wherein R₂ is hydroxyl and X is trans-CH=CH—.

163. 2-Decarboxy-2-aminomethyl-2,3-didehydro-19(R)-19-hydroxy-9-deoxo-9-methylene-PGE₁, a compound according to claim 162.

164. 2-Decarboxy-2-aminomethyl-2,3-didehydro-19(R)-19-hydroxy-9-deoxo-9-methylene-16,16-difluoro-PGE₁, a compound according to claim 162.

165. 2-Decarboxy-2-aminomethyl-2,3-didehydro-19(R)-19-hydroxy-9-deoxo-9-methylene-15(S)-15-methyl-PGE₁, a compound according to claim 162.

166. A compound according to claim 161, wherein R₂ is hydrogen and X is trans-CH=CH—.

167. 2-Decarboxy-2-aminomethyl-2,3-didehydro-19(R)-19-hydroxy-9-deoxo-9-methylene-11-deoxy-PGE₁, a compound according to claim 166.

168. 2-Decarboxy-2-aminomethyl-2,3-didehydro-19(R)-19-hydroxy-9-deoxo-9-methylene-11-deoxy-16,16-difluoro-PGE₁, a compound according to claim 166.

169. 2-Decarboxy-2-aminomethyl-2,3-didehydro-19(R)-19-hydroxy-9-deoxo-9-methylene-11-deoxy-15(S)-15-methyl PGE₁, a compound according to claim 166.

170. A compound according to claim 161, wherein R₂ is hydroxymethyl, and X is trans-CH=CH—.

171. 2-Decarboxy-2-aminomethyl-2,3-didehydro-19(R)-19-hydroxy-9-deoxo-9-methylene-11α-hydroxymethyl-PGE₁, a compound according to claim 170.

172. 2-Decarboxy-2-aminomethyl-2,3-didehydro-19(R)-19-hydroxy-9-deoxo-9-methylene-11-deoxy-11α-hydroxymethyl-16,16-difluoro-PGE₁, a compound according to claim 170.

173. 2-Decarboxy-2-aminomethyl-2,3-didehydro-19(R)-19-hydroxy-9-deoxo-9-methylene-11-deoxy-11α-hydroxymethyl-15-(S)-15-methyl-PGE₁, a compound according to claim 170.

174. A compound according to claim 2, wherein D is —(CH₂)₃—(CH₂)g—CH₂—, wherein g is zero, one, two or three.

175. A compound according to claim 174, wherein g is one.

176. A compound according to claim 175, wherein W is

177. A compound according to claim 176, wherein R₂ is hydroxyl.

178. A compound according to claim 177, wherein X is trans-CH=CH—.

179. 2-Decarboxy-2-aminomethyl-19(R)-19-hydroxy-PGF$_{1\alpha}$, a compound according to claim 178.

180. 2-Decarboxy-2-aminomethyl-16,16-dimethyl-19(R)-19-hydroxy-PGE$_{1\alpha}$, a compound according to claim 178.

181. 2-Decarboxy-2-aminomethyl-16,16-difluoro-19(R)-19-hydroxy-PGF$_{1\alpha}$, a compound according to claim 178.

182. A compound according to claim 177, wherein X is —CH$_2$CH$_2$—.

183. 2-Decarboxy-2-aminomethyl-13,14-dihydro-19(R)-19-hydroxy-PGF$_{1\alpha}$, a compound according to claim 182.

184. A compound according to claim 176, wherein R$_2$ is hydrogen.

185. A compound according to claim 184, wherein X is trans-CH=CH—.

186. 2-Decarboxy-2-aminomethyl-11-deoxy-19(R)-hydroxy-PGF$_{1\alpha}$, a compound according to claim 185.

187. 2-Decarboxy-2-aminomethyl-11-deoxy-16,16-dimethyl-19(R)-19-hydroxy-PGF$_{1\alpha}$, a compound according to claim 185.

188. 2-Decarboxy-2-aminomethyl-11-deoxy-16,16-difluoro-19(R)-19-hydroxy-PGF$_{1\alpha}$, a compound according to claim 185.

189. A compound according to claim 184, wherein X is —CH$_2$CH$_2$—.

190. 2-Decarboxy-2-aminomethyl-11-deoxy-13,14-dihydro-19-(R)-19-hydroxy-PGF$_{1\alpha}$, a compound according to claim 189.

191. A compound according to claim 176, wherein R$_2$ is hydroxymethyl.

192. A compound according to claim 191, wherein X is trans-CH=CH—.

193. 2-Decarboxy-2-aminomethyl-11-deoxy-11α-hydroxymethyl-19(R)-hydroxy-PGF$_{1\alpha}$, a compound according to claim 192.

194. 2-Decarboxy-2-aminomethyl-11-deoxy-11α-hydroxymethyl-16,16-dimethyl-19(R)-19-hydroxy-PGF$_{1\alpha}$, a compound according to claim 192.

195. 2-Decarboxy-2-aminomethyl-11-deoxy-11α-hydroxymethyl-16,16-difluoro-19(R)-19-hydroxy-PGF$_{1\alpha}$, a compound according to claim 192.

196. A compound according to claim 191, wherein X is —CH$_2$CH$_2$—.

197. 2-Decarboxy-2-aminomethyl-11-deoxy-11α-hydroxymethyl-13,14-dihydro-19(R)-19-hydroxy-PGF$_{1\alpha}$, a compound according to claim 196.

198. A compound according to claim 175, wherein W is

199. A compound according to claim 198, wherein R$_2$ is hydroxyl.

200. A compound according to claim 199, wherein X is trans-CH=CH—.

201. 2-Decarboxy-2-aminomethyl-19(R)-19-hydroxy-PGF$_{1\beta}$, a compound according to claim 200.

202. 2-Decarboxy-2-aminomethyl-16,16-dimethyl-19(R)-19-hydroxy-PGF$_{1\beta}$, a compound according to claim 200.

203. 2-Decarboxy-2-aminomethyl-16,16-difluoro-19(R)-19-hydroxy-PGF$_{1\beta}$, a compound according to claim 200.

204. A compound according to claim 199, wherein X is —CH$_2$CH$_2$—.

205. 2-Decarboxy-2-aminomethyl-13,14-dihydro-19(R)-19-hydroxy-PGF$_{2\beta}$, a compound according to claim 204.

206. A compound according to claim 198, wherein R$_2$ is hydrogen.

207. A compound according to claim 206, wherein X is trans-CH=CH—.

208. 2-Decarboxy-2-aminomethyl-11-deoxy-19(R)-19-hydroxy-PGF$_{1\beta}$, a compound according to claim 207.

209. 2-Decarboxy-2-aminomethyl-11-deoxy-16,16-dimethyl-19(R)-19-hydroxy-PGF$_{1\beta}$, a compound according to claim 207.

210. 2-Decarboxy-2-aminomethyl-16,16-difluoro-19(R)-19-hydroxy-PGF$_{1\beta}$, a compound according to claim 207.

211. A compound according to claim 206, wherein X is —CH$_2$CH$_2$—.

212. 2-Decarboxy-2-aminomethyl-11-deoxy-13,14-dihydro-19-(R)-19-hydroxy-PGF$_{1\beta}$, a compound according to claim 211.

213. A compound according to claim 198, wherein R$_2$ is hydroxymethyl.

214. A compound according to claim 213, wherein X is trans-CH=CH—.

215. 2-Decarboxy-2-aminomethyl-11-deoxy-11α-hydroxymethyl-19(R)-19-hydroxy-PGF$_{1\beta}$, a compound according to claim 214.

216. 2-Decarboxy-2-aminomethyl-11-deoxy-11α-hydroxymethyl-16,16-dimethyl-19(R)-19-hydroxy-PGF$_{1\beta}$, a compound according to claim 214.

217. 2-Decarboxy-2-aminomethyl-11-deoxy-11α-hydroxymethyl-16,16-difluoro-19(R)-19-hydroxy-PGF$_{1\beta}$, a compound according to claim 214.

218. A compound according to claim 213, wherein X is —CH$_2$CH$_2$—.

219. 2-Decarboxy-2-aminomethyl-11-deoxy-11α-hydroxymethyl-13,14-dihydro-19(R)-19-hydroxy-PGF$_{1\beta}$, a compound according to claim 218.

220. A compound according to claim 175, wherein W is

221. A compound according to claim 220, wherein R$_2$ is hydroxyl.

222. A compound according to claim 221, wherein X is trans-CH=CH—.

223. 2-Decarboxy-2-aminomethyl-19(R)-19-hydroxy-PGE$_1$, a compound according to claim 222.

224. 2-Decarboxy-2-aminomethyl-16,16-dimethyl-19(R)-19-hydroxy-PGE$_1$, a compound according to claim 222.

225. 2-Decarboxy-2-aminomethyl-16,16-difluoro-19(R)-19-hydroxy-PGE$_1$, a compound according to claim 222.

226. A compound according to claim 221, wherein X is —CH$_2$CH$_2$—.

227. 2-Decarboxy-2-aminomethyl-13,14-dihydro-19(R)-19-hydroxy-PGE$_1$, a compound according to claim 226.

228. A compound according to claim 220, wherein $R_2$ is hydrogen.

229. A compound according to claim 228, wherein X is trans-CH=CH—.

230. 2-Decarboxy-2-aminomethyl-11-deoxy-19(R)-19-hydroxy-PGE$_1$, a compound according to claim 229.

231. 2-Decarboxy-2-aminomethyl-11-deoxy-16,16-dimethyl-19(R)-19-hydroxy-PGE$_1$, a compound according to claim 229.

232. 2-Decarboxy-2-aminomethyl-11-deoxy-16,16-difluoro-19(R)-19-hydroxy-PGE$_1$, a compound according to claim 229.

233. A compound according to claim 228, wherein X is —CH$_2$CH$_2$—.

234. 2-Decarboxy-2-aminomethyl-11-deoxy-13,14-dihydro-19-(R)-19-hydroxy-PGE$_1$, a compound according to claim 233.

235. A compound according to claim 220, wherein $R_2$ is hydroxymethyl.

236. A compound according to claim 235, wherein X is trans-CH=CH—.

237. 2-Decarboxy-2-aminomethyl-11-deoxy-11α-hydroxymethyl-19(R)-19-hydroxy-PGE$_1$, a compound according to claim 236.

238. 2-Decarboxy-2-aminomethyl-11-deoxy-11α-hydroxymethyl-16,16-dimethyl-19(R)-19-hydroxy-PGE$_1$, a compound according to claim 236.

239. 2-Decarboxy-2-aminomethyl-11-deoxy-11α-hydroxymethyl-16,16-difluoro-19(R)-19-hydroxy-PGE$_1$, a compound according to claim 236.

240. A compound according to claim 235, wherein X is —CH$_2$CH$_2$—.

241. 2-Decarboxy-2-aminomethyl-11-deoxy-11α-hydroxymethyl-13,14-dihydro-19(R)-19-hydroxy-PGE$_1$, a compound according to claim 240.

242. A compound according to claim 175, wherein W is

243. A compound according to claim 242, wherein $R_2$ is hydroxyl.

244. A compound according to claim 243, wherein X is trans-CH=CH—.

245. 2-Decarboxy-2-aminomethyl-9-deoxo-9-methylene-19(R)-19-hydroxy-PGE$_1$, a compound according to claim 244.

246. 2-Decarboxy-2-aminomethyl-9-deoxo-9-methylene-16,16-dimethyl-19(R)-19-hydroxy-PGE$_1$, a compound according to claim 244.

247. 2-Decarboxy-2-aminomethyl-9-deoxo-9-methylene-16,16-difluoro-19(R)-19-hydroxy-PGE$_1$, a compound according to claim 244.

248. A compound according to claim 243, wherein X is —CH$_2$CH$_2$—.

249. 2-Decarboxy-2-aminomethyl-9-deoxo-9-methylene-13,14-dihydro-19(R)-19-hydroxy-PGE$_1$, a compound according to claim 248.

250. A compound according to claim 242, wherein $R_2$ is hydrogen.

251. A compound according to claim 250, wherein X is trans-CH=CH—.

252. 2-Decarboxy-2-aminomethyl-9-deoxo-9-methylene-11-deoxy-19(R)-19-hydroxy-PGE$_1$, a compound according to claim 251.

253. 2-Decarboxy-2-aminomethyl-9-deoxo-9-methylene-11-deoxy-16,16-dimethyl-19(R)-19-hydroxy-PGE$_1$, a compound according to claim 251.

254. 2-Decarboxy-2-aminomethyl-9-deoxo-9-methylene-11-deoxy-16,16-difluoro-19(R)-19-hydroxy-PGE$_1$, a compound according to claim 251.

255. A compound according to claim 250, wherein X is —CH$_2$CH$_2$—.

256. 2-Decarboxy-2-aminomethyl-9-deoxo-9-methylene-11-deoxy-13,14-dihydro-19(R)-19-hydroxy-PGE$_1$, a compound according to claim 255.

257. A compound according to claim 242, wherein $R_2$ is hydroxymethyl.

258. A compound according to claim 257, wherein X is trans-CH=CH—.

259. 2-Decarboxy-2-aminomethyl-9-deoxo-9-methylene-11-deoxy-11α-hydroxymethyl-19(R)-19-hydroxy-PGE$_1$, a compound according to claim 258.

260. 2-Decarboxy-2-aminomethyl-9-deoxo-9-methylene-11-deoxy-11α-hydroxymethyl-16,16-dimethyl-19(R)-19-hydroxy-PGE$_1$, a compound according to claim 258.

261. 2-Decarboxy-2-aminomethyl-9-deoxo-9-methylene-11-deoxy-11α-hydroxymethyl-16,16-difluoro-19(R)-19-hydroxy-PGE$_1$, a compound according to claim 258.

262. A compound according to claim 257, wherein X is —CH$_2$CH$_2$—.

263. 2-Decarboxy-2-aminomethyl-9-deoxo-9-methylene-11-deoxy-11α-hydroxymethyl-13,14-dihydro-19(R)-19-hydroxy-PGE$_1$, a compound according to claim 262.

* * * * *

UNITED STATES PATENT AND TRADEMARK OFFICE
CERTIFICATE OF CORRECTION

PATENT NO. : 4,283,558                             Page 1 of 2

DATED : 11 August 1981

INVENTOR(S) : John C. Sih

It is certified that error appears in the above—identified patent and that said Letters Patent is hereby corrected as shown below:

Column 5, line 24, "-PGFxzl," should read -- -PGF$_1$ --.
Column 7, line 62, "19(R)-hydroxy-" should read -- -19(R)-19-hydroxy- --.
Column 11, line 53, "claim 105" should read -- claim 104 --.
Column 11, line 62, "-9-methylene-15(S)-" should read -- -9-methylene-11-deoxy-15(S)- --.
Column 12, line 21, "-hydroxy-methyl-" should read -- -hydroxymethyl- --.
Column 12, line 25, "-16,-16-" should read -- -16,16- --.
Column 15, line 6, "-hydroxy-PGE$_1$α," should read -- -hydroxy-PGF$_1$α, --.
Column 16, line 19, "-aminomethyl-16,16-" should read -- -aminomethyl-11-deoxy-16,16- --.

UNITED STATES PATENT AND TRADEMARK OFFICE
CERTIFICATE OF CORRECTION

PATENT NO. : 4,283,558

DATED : 11 August 1981

INVENTOR(S) : John C. Sih

It is certified that error appears in the above—identified patent and that said Letters Patent is hereby corrected as shown below:

Column 14, line 46, "-methylene-11α-" should read -- -methylene-11-deoxy-11α- --.

Signed and Sealed this

Seventeenth Day of November 1981

[SEAL]

Attest:

Attesting Officer

GERALD J. MOSSINGHOFF

Commissioner of Patents and Trademarks